(12) United States Patent
Singh et al.

(10) Patent No.: US 7,495,025 B2
(45) Date of Patent: Feb. 24, 2009

(54) SPIRO-1,2,4-TRIOXANES

(75) Inventors: Chandan Singh, Lucknow (IN); Heetika Malik, Lucknow (IN); Sunil Kumar Puri, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/514,453

(22) Filed: Sep. 1, 2006

(65) Prior Publication Data

US 2007/0191475 A1    Aug. 16, 2007

(30) Foreign Application Priority Data

Dec. 30, 2005    (IN)    .................. 3516/DEL/2005

(51) Int. Cl.
*A61K 31/357* (2006.01)
*C07D 323/06* (2006.01)

(52) U.S. Cl. ........................ 514/452; 549/333

(58) Field of Classification Search ................ 514/452; 549/333

See application file for complete search history.

(56) References Cited

U.S. PATENT DOCUMENTS 6,316,493 B1 * 11/2001 Singh et al. ............... 514/452
6,737,438 B2 * 5/2004 Singh et al. ............... 514/452
7,071,226 B1 * 7/2006 Singh et al. ............... 514/452

FOREIGN PATENT DOCUMENTS

IN    0909/DEL/2003    7/2003
WO    WO 03/082852    10/2003
WO    WO 2006/070381    7/2006

OTHER PUBLICATIONS

Klayman, D. L *Science* 1985, 228, 1049.
Singh, C. *Tetrahedron Lett*. 1990, 31, 6901.
Singh, C.; Misra, D.; Saxena, G.; Chandra, S. *Bioorg. Med. Chem. Lett*. 1995, 5, 1913.
Bhattacharya, A. K.; Sharma, R. P. *Heterocycles* 1999, 51, 1681.
Borstnik, K.; Paik, I.; Shapiro, T. A.; Posner, G. H. *Int. J. Parasitol*. 2002, 32, 1661.
Ploypradith, P. *Acta Trop*. 2004, 89, 329.
O'Neill, P. M.; Posner, G. H. *J. Med. Chem*. 2004, 47, 2945.
Singh, C.; Malik, H.; Puri, S. K. *Bioorg. Med. Chem. Lett*. 2004, 14, 459.
Singh, C.; Gupta, N.; Puri, S. K. *Bioorg. Med. Chem*. 2004, 12, 5553.

* cited by examiner

*Primary Examiner*—Taofiq A Solola
(74) *Attorney, Agent, or Firm*—Kenyon & Kenyon LLP

(57) ABSTRACT

The present invention relates to spiro 1,2,4-trioxanes of general formula 4. This invention more particularly relates to a process for the preparation of a series of spiro 1,2,4-trioxanes.

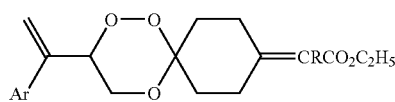

Wherein, Ar represents aryl groups such as phenyl, 4-biphenyl, 4-chlorophenyl, 4-methoxyphenyl, 4-methylphenyl, 4-cyclohexylphenyl, 1-naphthyl, 2-naphthyl and the like and R represents hydrogen or the alkyl group such as methyl, ethyl and the like. Several of these compounds show high order of antimalarial activity against multidrug-resistant malaria in mice and thus hold promise as antimalarial agents against multidrug-resistant malaria.

29 Claims, No Drawings

SPIRO-1,2,4-TRIOXANES

FIELD OF THE INVENTION

The present invention relates to novel spiro 1,2,4-trioxanes of general formula 4. This invention more particularly relates to a process for the preparation of a series of novel spiro 1,2,4-trioxanes.

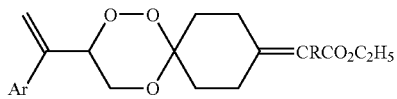

4

Wherein, Ar represents aryl groups such as phenyl, 4-biphenyl, 4-chlorophenyl, 4-methoxyphenyl, 4-methylphenyl, 4-cyclohexylphenyl, 1-naphthyl, 2-naphthyl and the like and R represents hydrogen or the alkyl group such as methyl, ethyl and the like. Several of these novel compounds show high order of antimalarial activity against multidrug-resistant malaria in mice and are useful as antimalarial agents against multidrug-resistant malaria.

BACKGROUND OF INVENTION

Malaria is a parasitic disease which is caused by various species of *Plasmodium* protozoa. Together with AIDS and TB, malaria is responsible for largest number of deaths annually. The high rate of mortality associated with malaria can be attributed to the increasing cases of resistance of *Plasmodium falciparum*, the most deadly of the four human infecting malarial parasites, to the contemporary antimalarial drugs. Chloroquine is one of the most inexpensive, readily available, and probably most prescribed drugs for the chemotherapy of malaria, it has been rendered ineffective in many parts of the world, due to the emergence of multidrug-resistant *P. falciparum*. Against this background, discovery of artemisinin as the active principle of Chinese traditional drug against malaria, *Artemisia annua*, is an important milestone in malaria chemotherapy. Artemisinin is active against both chloroquine sensitive and chloroquine resistant malaria.

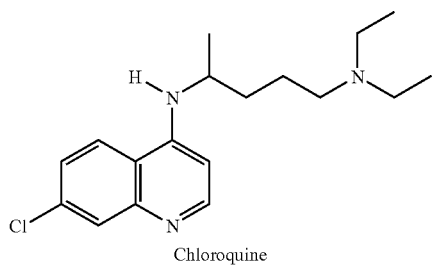

Chloroquine

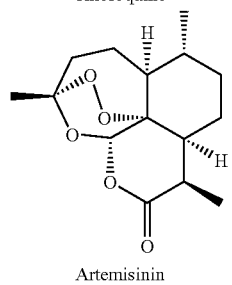

Artemisinin

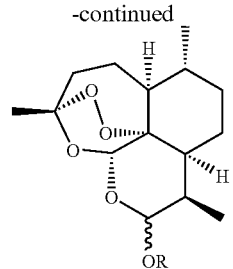

Artemether R = Me
Arteether R = Et

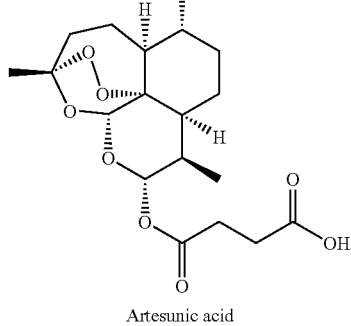

Artesunic acid

Semisynthetic derivatives of artemisinin such as arteether, artemether and artesunic acid, are several times more potent than the parent compound.

The limited availability of artemisinin from malaria such as cerebral malaria [For reviews on artemisinin and its analogues see: (a) Klayman, D. L *Science* 1985, 228, 1049. (b) Bhattacharya, A. K.; Sharma, R. P. *Heterocycles* 1999, 51, 1681. (c) Borstnik, K.; Paik, I.; Shapiro, T. A.; Posner, G. H. *Int. J Parasitol.* 2002, 32, 1661. (d) Ploypradith, P. *Acta Trop.* 2004, 89, 329. (e) O'Neill, P. M.; Posner, G. H. *J. Med. Chem.* 2004, 47, 2945].natural source and recognition of endoperoxide linkage in the form of a 1,2,4-trioxane ring system as the antimalarial pharmacophore of these compounds, has led to the present efforts to develop structurally simple synthetic trioxanes as substitutes of artemisinin derivatives. Several of these synthetic 1,2,4-trioxanes have shown promising antimalarial activity [(a) Bhattacharya, A. K.; Sharma, R. P. *Heterocycles* 1999, 51, 1681. (b) Borstnik, K.; Paik, I.; Shapiro, T. A.; Posner, G. H. *Int. J. Parasitol.* 2002, 32, 1661. (c) Singh, C.; Misra, D.; Saxena, G.; Chandra, S. *Bioorg. Med. Chem. Lett.* 1995, 5, 1913. (d) Singh, C.; Puri, S. K. U.S. Pat. No. 6,316,493 B1, 2001. (e) Singh, C.; Malik, H.; Puri, S. K. *Bioorg. Med. Chem. Lett.* 2004, 14, 459. (f) Singh, C.; Gupta, N.; Puri, S. K. *Bioorg. Med. Chem.* 2004, 12, 5553. (g) Singh, C.; Tiwari, P.; Puri, S. K. PCT Patent application No. PCT/1N02/00093, dated Mar. 28, 2002. (h) Singh, C. Malik, H.; Puri, S. K. PCT Patent application No. PCT/1N04/00413, dated Dec. 27, 2004].

SUMMARY OF THE INVENTION

A main objective of the present invention is to provide a novel spiro 1,2,4-trioxanes useful for treating malaria.

The objective of the present invention is also to provide a process for the preparation of novel spiro 1,2,4-trioxanes of general formula 4, a new series of antimalarial agents.

Another objective of the present invention is to provide a pharmaceutical composition comprising a spiro 1,2,4-trioxane of general formula 4 for the treatment of malaria.

Still another objective of the present invention is to provide the novel compounds compounds of general formula 4 which are useful for the treatment of multidrug resistance malaria.

Accordingly, the present invention provides a novel spiro 1,2,4-trioxane of general formula 4 below:

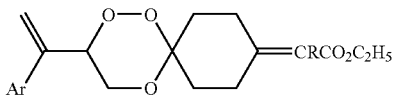

Wherein, Ar represents an aryl group, and R represents hydrogen or an alkyl group. Preferably, the aryl group is an unsubstituted or substituted aromatic hydrocarbon, wherein the substituted aromatic hydrocarbon is substituted with at least one substituent selected from the group consisting of a $C_1$-$C_6$ alkyl, a $C_3$-$C_8$ cycloalkyl, a $C_1$-$C_6$ alkoxy, a halogen and an aromatic hydrocarbon group.

In an embodiment of the present invention the compound of general 4 is selected from [3-(1-Phenyl-vinyl)-1,2,5-trioxa-spiro[5.5]undec-9-ylidene]-acetic acid ethyl ester 4aa,2-[3-(1-Phenyl-vinyl)-1,2,5-trioxa-spiro[5.5]undec-9-ylidene]-propionic acid ethyl 4ba,2-[3-(1-Phenyl-vinyl)-1,2,5-trioxa-spiro[5.5]undec-9-ylidene]-butyric acid ethyl ester 4ca,[3-(1-Biphenyl-4-yl-vinyl)-1,2,5-trioxa-spiro[5.5]undec-9-ylidene]-acetic acid ethyl ester 4ab,2-[3-(1-Biphenyl-4-yl-vinyl)-1,2,5-trioxa-spiro[5.5]undec-9-ylidene]-propionic acid ethyl ester 4bb,{3-[1-(4-Chloro-phenyl)-vinyl]-1,2,5-trioxa-spiro[5.5]undec-9-ylidene}-acetic acid ethyl ester 4ac,2-{3-[1-(4-Chloro-phenyl)-vinyl]-1,2,5-trioxa-spiro[5.5]undec-9-ylidene}-propionic acid ethyl ester 4bc,{3-[1-(4-Methoxy-phenyl)-vinyl]-1,2,5-trioxa-spiro[5.5]undec-9-ylidene}-acetic acid ethyl ester 4ad,2-{3-[1-(4-Methoxy-phenyl)-vinyl]-1,2,5-trioxa-spiro[5.5]undec-9-ylidene}-propionic acid ethyl ester 4bd,[3-(1-p-Tolyl-vinyl)-1,2,5-trioxa-spiro[5.5]undec-9-ylidene]-acetic acid ethyl ester 4ae, 2-[3-(1-p-Tolyl-vinyl)-1,2,5-trioxa-spiro[5.5]undec-9-ylidene]-propionic acid ethyl ester 4be, {3-[1-(4-Cyclohexyl-phenyl)-vinyl]-1,2,5-trioxa-spiro[5.5]undec-9-ylidene}-acetic acid ethyl ester 4af,2-{3-[1-(4-Cyclohexyl-phenyl)-vinyl]-1,2,5-trioxa-spiro[5.5]undec-9-ylidene}-propionic acid ethyl ester 4bf, [3-(1-Naphthalen-1-yl-vinyl)-1,2,5-trioxa-spiro[5.5]undec-9-ylidene]-acetic acid ethyl ester 4ag,2-[3-(1-Naphthalen-1-yl-vinyl)-1,2,5-trioxa-spiro[5.5]undec-9-ylidene]-propionic acid ethyl ester 4bg, [3-(1-Naphthalen-2-yl-vinyl)-1,2,5-trioxa-spiro[5.5]undec-9-ylidene]-acetic acid ethyl ester 4ah,2-[3-(1-Naphthalen-2-yl-vinyl)-1,2,5-trioxa-spiro[5.5]undec-9-ylidene]-propionic acid ethyl ester 4bh.

In yet another embodiment of the invention there is provided a novel Spiro 1,2,4-trioxane wherein the Ar is selected from the group consisting of phenyl, 4-biphenyl, 4-chlorophenyl, 4-methoxyphenyl, 4-methylphenyl, 4-cyclohexylphenyl, 1-naphthyl, and 2-naphthyl.

In yet another embodiment of the invention there is provided a novel spiro 1,2,4-trioxane, wherein the alkyl group is selected from methyl, ethyl, and propyl.

In still another embodiment of the invention there is provided a novel spiro 1,2,4-trioxanes wherein the structural formulas of said compounds are given below:

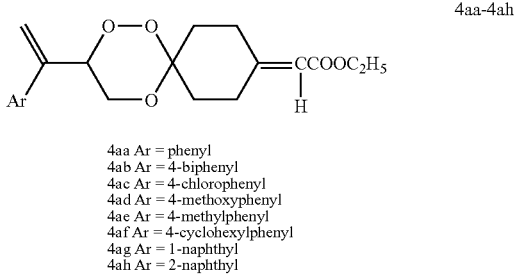

4aa Ar = phenyl
4ab Ar = 4-biphenyl
4ac Ar = 4-chlorophenyl
4ad Ar = 4-methoxyphenyl
4ae Ar = 4-methylphenyl
4af Ar = 4-cyclohexylphenyl
4ag Ar = 1-naphthyl
4ah Ar = 2-naphthyl wherein, the compounds obtained can be represented by the following chemical names:
4aa=[3-(1-Phenyl-vinyl)-1,2,5-trioxa-spiro[5.5]undec-9-ylidene]-aceticacid ethyl ester,
4ab=[3-(1-Biphenyl-4-yl-vinyl)-1,2,5-trioxa-spiro[5.5]undec-9-ylidene]-acetic acid ethyl ester,
4ac={3-[1-(4-Chloro-phenyl)-vinyl]-1,2,5-trioxa-spiro[5.5]undec-9-ylidene}-acetic acid ethyl ester,
4ad={3-[1-(4-Methoxy-phenyl)-vinyl]-1,2,5-trioxa-spiro[5.5]undec-9-ylidene}-aceticacid ethyl ester,
4ae=[3-(1-p-Tolyl-vinyl)-1,2,5-trioxa-spiro[5.5]undec-9-ylidene]-acetic acid ethyl ester,
4af={3-[1-(4-Cyclohexyl-phenyl)-vinyl]-1,2,5-trioxa-spiro[5.5]undec-9-ylidene}-acetic acid ethyl ester,
4ag=[3-(1-Naphthalen-1-yl-vinyl)-1,2,5-trioxa-spiro[5.5]undec-9-ylidene]-acetic acid ethyl ester,
4ah=[3-(1-Naphthalen-2-yl-vinyl)-1,2,5-trioxa-spiro[5.5]undec-9-ylidene]-acetic acid ethyl ester.

In still another embodiment of the invention there are provided novel spiro 1,2,4-trioxanes wherein the structural formulas of said compounds are given below:

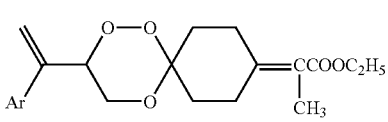

4ba Ar = phenyl
4bb Ar = 4-biphenyl
4bc Ar = 4-chlorophenyl
4bd Ar = 4-methoxyphenyl
4be Ar = 4-methylphenyl
4bf Ar = 4-cyclohexylphenyl
4bg Ar = 1-naphthyl
4bh Ar = 2-naphthyl wherein, the compounds obtained can be represented by the following chemical names:
4ba=2-[3-(1-Phenyl-vinyl)-1,2,5-trioxa-spiro[5.5]undec-9-ylidene]-propionic acid ethyl,
4bb=2-[3-(1-Biphenyl-4-yl-vinyl)-1,2,5-trioxa-spiro[5.5]undec-9-ylidene]-propionic acid ethyl ester,
4bc=2-{3-[1-(4-Chloro-phenyl)-vinyl]-1,2,5-trioxa-spiro[5.5]undec-9-ylidene}-propionic acid ethyl ester,
4bd=2-{3-[1-(4-Methoxy-phenyl)-vinyl]-1,2,5-trioxa-spiro[5.5]undec-9-ylidene}-propionic acid ethyl ester,
4be=2-[3-(1-p-Tolyl-vinyl)-1,2,5-trioxa-spiro[5.5]undec-9-ylidene]-propionic acid ethyl ester,
4bf=2-{3-[1-(4-Cyclohexyl-phenyl)-vinyl]-1,2,5-trioxaspiro[5.5]undec-9-ylidene}-propionic acid ethyl ester,
4bg=2-[3-(1-Naphthalen-1-yl-vinyl)-1,2,5-trioxa-spiro[5.5]undec-9-ylidene]-propionic acid ethyl ester,
4bh=2-[3-(1-Naphthalen-2-yl-vinyl)-1,2,5-trioxa-spiro[5.5]undec-9-ylidene]-propionic acid ethyl ester.

In still another embodiment of the invention there is provided a novel spiro 1,2,4-trioxane having a structural formula of 4ca is given below:

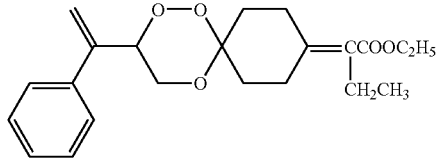

4ca

In yet another embodiment of the invention there is provided a novel compound of general formula 4 as in claim 1, wherein the compound is effective against parasitaemia upto 100%.

In yet another embodiment of the invention a compound of formula 4 is used for the treatment of malaria.

Accordingly, the present invention provides a process for the preparation of novel spiro 1,2,4-trioxanes of general formula 4

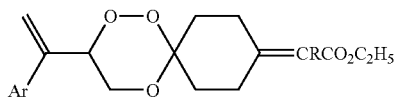

4 wherein, Ar represents an aryl group, and R represents hydrogen or an alkyl group. Preferably, the Aryl group is an unsubstituted or substituted aromatic hydrocarbon, wherein the substituted aromatic hydrocarbon is substituted with at least one substituent selected from the group consisting of a $C_1$-$C_6$ alkyl, a $C_3$-$C_8$ cycloalkyl, a $C_1$-$C_6$ alkoxy, a halogen and an aromatic hydrocarbon group.

In an embodiment of the invention there is provided a novel process for the preparation of a spiro 1,2,4-trioxane of general formula 4 comprising the steps of:

(a) photooxygenating an allylic alcohol of formula 1, wherein formulas 1a to 1e are preferred examples, in the presence of a sensitizer and a light source which provides visible light, in an organic solvent at a temperature ranging from −10° C. to 0° C. to obtain a β-hydroxyhydroperoxide of formula 2, wherein formulas 2a to 2e are preferred examples,

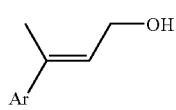

1

1a; Ar = Phenyl
1b; Ar = 4-Biphenyl
1c; Ar = 4-chlorophenyl
1d; Ar = 4-methoxyphenyl
1e; Ar = 4-methylphenyl

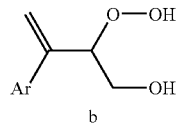

2

2a; Ar = Phenyl
2b; Ar = 4-Biphenyl
2c; Ar = 4-chlorophenyl
2d; Ar = 4-methoxyphenyl
2e; Ar = 4-methylphenyl (b) reacting a β-hydroxyhydroperoxide of formula 2 in-situ with 1,4-cyclohexanedione in the presence of an acid catalyst at temperature 0° C. to for 18 hours to obtain keto trioxanes of general formula 3, wherein 3a to 3e are preferred examples

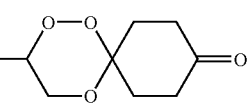

3

3a; Ar = Phenyl
3b; Ar = 4-Biphenyl
3c; Ar = 4-chlorophenyl
3d; Ar = 4-methoxyphenyl
3e; Ar = 4-methylphenyl (c) reacting the keto trioxanes of step (b) with triethylphosphonoacetate or substituted triethylphosphonoacetate in the presence of a base in an organic solvent at a temperature ranging from 0° C. to 50° C. to obtain the spiro 1,2,4-trioxane of formula 4,

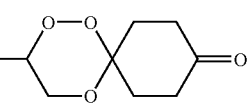

4

(d) isolating and purifying by conventional methods to furnish the spiro 1,2,4-trioxane of formula 4.

In yet another embodiment of the invention wherein the organic solvent in step (a) is selected from aprotic solvents such as acetonitrile.

In yet another embodiment of the invention, the substituted triethylphosphonoacetate is selected from triethylphosphono-2-propionate, triethylphosphono-2-butyrate.

In yet another embodiment of the invention, the base in step (c) is selected from sodium hydride, and n-butyl lithium.

In yet another embodiment of the invention, the organic solvent used in step (c) is selected from tetrahydrofuran, dimethoxyetthane, and diethyl ether.

In still another embodiment of the invention, the acid catalyst used in step (b) is selected from hydrogen chloride and p-toluene sulfonic acid.

In still another embodiment of the invention, the spiro 1,2,4-trioxanes of formula 4 obtained by the above process of the invention are represented by the following compounds:

4aa=[3-(1-Phenyl-vinyl)-1,2,5-trioxa-spiro[5.5]undec-9-ylidene]-acetic acid ethyl ester, 4ba=2-[3-(1-Phenyl-vinyl)-1,2,5-trioxa-spiro[5.5]undec-9-ylidene]-propionic acid ethyl ester, 4ca=2-[3-(1-Phenyl-vinyl)-1,2,5-trioxa-spiro[5.5]undec-9-ylidene]-butyric acid ethyl ester,
4ab=[3-(1-Biphenyl-4-yl-vinyl)-1,2,5-trioxa-spiro[5.5]undec-9-ylidene]-acetic acid ethyl ester,
4bb=2-[3-(1-Biphenyl-4-yl-vinyl)-1,2,5-trioxa-spiro[5.5]undec-9-ylidene]-propionic acid ethyl ester,
4ac={3-[1-(4-Chloro-phenyl)-vinyl]-1,2,5-trioxa-spiro[5.5]undec-9-ylidene}-acetic acid ethyl ester,
4bc=2-{3-[1-(4-Chloro-phenyl)-vinyl]-1,2,5-trioxa-spiro[5.5]undec-9-ylidene}-propionic acid ethyl ester,
4ad={3-[1-(4-Methoxy-phenyl)-vinyl]-1,2,5-trioxa-spiro[5.5]undec-9-ylidene}-acetic acid ethyl ester,
4bd=2-{3-[1-(4-Methoxy-phenyl)-vinyl]-1,2,5-trioxa-spiro[5.5]undec-9-ylidene}-propionic acid ethyl ester,
4bd=[3-(1-p-Tolyl-vinyl)-1,2,5-trioxa-spiro[5.5]undec-9-ylidene]-acetic acid ethyl ester,
4be=2-[3-(1-p-Tolyl-vinyl)-1,2,5-trioxa-spiro[5.5]undec-9-ylidene]-propionic acid ethyl ester,
4af={3-[1-(4-Cyclohexyl-phenyl)-vinyl]-1,2,5-trioxa-spiro[5.5]undec-9-ylidene}-acetic acid ethyl ester,
4af=2-{3-[1-(4-Cyclohexyl-phenyl)-vinyl]-1,2,5-trioxa-spiro[5.5]undec-9-ylidene}-propionic acid ethyl ester,
4ag=[3-(1-Naphthalen-1-yl-vinyl)-1,2,5-trioxa-spiro[5.5]undec-9-ylidene]-acetic acid ethyl ester,
4ag=2-[3-(1-Naphthalen-1-yl-vinyl)-1,2,5-trioxa-spiro[5.5]undec-9-ylidene]-propionic acid ethyl ester,
4ah=[3-(1-Naphthalen-2-yl-vinyl)-1,2,5-trioxa-spiro[5.5]undec-9-ylidene]-acetic acid ethyl ester,
4bh=2-[3-(1-Naphthalen-2-yl-vinyl)-1,2,5-trioxa-spiro[5.5]undec-9-ylidene]-propionic acid ethyl ester.

One of the features of the present invention is a pharmaceutical composition comprising a pharmaceutically effective amount of a compound of formula 4, optionally with at least one of pharmaceutically acceptable diluents and/or carrier.

In an embodiment of the present invention there is provided a pharmaceutical composition useful in the treatment of malaria.

In an embodiment of the present invention there is provided a pharmaceutical composition wherein the dose of composition is in the range between 24 to 96 mg/kg/day.

In still another embodiment of the invention, the pharmaceutical composition is useful for treatment of multidrug resistance malaria.

In still another embodiment of the invention, the pharmaceutical composition is administered intramuscularly, oral route or intraperitoneally.

In still another embodiment of the invention, the composition is effective against parasaitemia upto 100%.

Another feature of the invention is a method of treating a subject having malaria, comprising administering to the subject a pharmaceutically effective amount of a composition containing compound of formula 4,

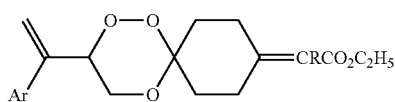

4 or a pharmaceutically acceptable salt thereof, wherein Ar represent an aryl group such as phenyl, 4-biphenyl, 4-chlorophenyl, 4-methoxyphenyl, 4-methylphenyl, 4-cyclohexylphenyl, 1-naphthyl, and 2-naphthyl. R represents hydrogen or an alkyl group such as methyl, ethyl, propyl.

In yet another embodiment of the invention, the composition is administered intramuscularly, intraperitoneally, or orally.

In yet another embodiment of the invention, the pharmaceutically acceptable amount of the compound of formula 4 is in the range of 24 to 96 mg of the compound of formula 4 per kilogram of body weight of subject per day.

In still another embodiment of the invention, the subject is a human being.

DETAILED DESCRIPTION OF THE INVENTION

In the process for preparing spiro 1,2,4-trioxanes of the present invention, allylic alcohols of formula 1 can be prepared by known procedures [(a) Singh, C. *Tetrahedron Lett.* 1990, 31, 6901. (b) Singh, C.; Tiwari, P.; Puri, S. K. PCT Patent application No. PCT/1N02/00093, dated 28 Mar. 2002. (c) Singh, C.; Kanchan, R.; Chandra, S. and Puri, S. K. Indian patent application no. 0909/DEL/2003 dated 18 Jul. 2003].

In the process for preparing spiro 1,2,4-trioxanes of the present invention, photooxygenation of allylic alcohols of formula 1 may be effected by passing oxygen gas or air in the solution of the alcohol in an organic solvent and in the presence of a sensitizer and a light source which provides visible light, to furnish β-hydroxyhydroperoxide of formula 2. The sensitizer can be a compound which increases the sensitivity of the photooxygenation for light from the light source and can be a dye such as methylene blue. These β-hydroxyhydroperoxide of formula 2 are known compounds as they have been prepared earlier [(a) Singh, C. *Tetrahedron Lett.* 1990, 31, 6901. (b) Singh, C.; Tiwari, P.; Puri, S. K. PCT Patent application No. PCT/1N02/00093, dated 28 Mar. 2002. (c) Singh, C.; Kanchan, R.; Chandra, S. and Puri, S. K. Indian patent application no. 0909/DEL/2003 dated 18 Jul. 2003].

In the process for preparing spiro 1,2,4-trioxanes of the present invention, reaction of β-hydroxyhydroperoxide of formula 2 with 1,4-cyclohexanedione in presence of an acid catalyst such as concd HCl, p-toluene sulphonic acid (p-TSA) and the like at temperature ranging from 0° C. to r.t. furnish keto 1,2,4-trioxanes of formula 3. These trioxanes of formula 3 can be isolated and purified by standard laboratory methods such as column chromatography or crystallization. These compounds have been tested against malaria parasites in mice and show only moderate order of activity. Keto trioxanes 3a, 3b, 3c, 3d, 3e are known compounds [ (a) Singh, C.; Malik, H.; Puri, S. K. *Bioorg. Med. Chem. Lett.* 2004, 14, 459. (b) Singh, C.; Malik, H.; Puri, S. K. PCT Patent application No. PCT/1N04/00413, dated 27 Dec. 2004] while compounds 3f, 3g, 3 h are new compounds.

In the process for preparing spiro 1,2,4-trioxanes of the present invention, Witting olefination of keto trioxanes of formula 3 by reaction with triethylphosphonoacetate or substituted triethylphosphonoacetate such as triethylphosphono-2-propionate, triethylphosphono-2-butyrate in the presence of a base such as NaH, n-BuLi and the like, in an organic solvent such as dimethoxyethane, tetrahydrofuran and the like at temperature ranging from 0° C. to room temperature furnish spiro 1,2,4-trioxanes of formula 4. These spiro 1,2,4-trioxanes of formula 4 can be isolated and purified by standard laboratory methods such as column chromatography and crystallization. These spiro 1,2,4-trioxanes of formula 4 are new chemical entities and they have not been prepared earlier. These 1,2,4-trioxanes of formula 4 have been tested against malaria parasites in mice and have shown high order of antimalarial activity.

The disclosures of the prior art references referred to in this patent application are incorporated herein by reference. This invention is further illustrated by the following examples which should not, however, be construed to limit the scope of the present invention.

EXAMPLE 1

3-(1-Phenyl-vinyl)-1,2,5-trioxaspiro[5.5]undec-9-one (compound 3a, Ar=phenyl)

Allylic alcohol. A solution of allylic alcohol of 1a (1 g) and methylene blue (10 mg) in MeCN (50 mL) was photooxygenated at −10° C. to 0° C. for 4 h to give β-hydroxyhydroperoxide 2a which was reacted in situ with 1,4-cyclohexanedione (1.15 g) in presence of concd HCl (5 drops) for 18 h at 0° C. Reaction mixture was concentrated under reduced pressure and residue taken up in diethylether (100 mL) was washed with sat. aq NaHCO$_3$ (30 mL). The aqueous layer was extracted with diethylether (2×20 mL), combined organic layer was dried over anhyd. Na$_2$SO$_4$ and concentrated. The crude product was purified by column chromatography on silica gel to furnish trioxane 3a (0.94 g, 51% yield, based on allylic alcohol 1a used), m.p. 70-71° C. Trioxane 3a was obtained in 53% yield when β-hydroxyhydroperoxide 2a was reacted with 1,4-cyclohexanedione at r.t. for 8 h using p-toluene sulphonic acid (p-TSA) as acid catalyst.

[3-(1-Phenyl-vinyl)-1,2,5-trioxa-spiro[5.5]undec-9-ylidene]-acetic acid ethyl ester (compound 4aa, Formula 4, Ar=phenyl, R=H).

To a stirred and cooled (0° C.) mixture of NaH (0.2 g) in dry dimethoxyethane (15 mL) was added triethyl phosphonoacetate (1.2 g) and the reaction mixture was stirred at 0° C. for 1 h. To the solution thus obtained was added dropwise a solution of keto trioxane 3a (1 g) in dry dimethoxyethane (15 mL), while maintaining the temperature of the flask at 0° C. After the addition was complete the resulting solution was stirred for additional twenty minutes at 0° C. The reaction mixture was diluted with water (40 mL) and extracted with diethylether (2×75 mL). The combined organic layer was washed successively with water (2×15 mL) and brine, dried over anhyd Na$_2$SO$_4$, concentrated and purified by column chromatography over silica gel to furnish spiro trioxane 4aa (oil, 1.16 g, 92.8% yield) as a mixture of E and Z isomers.

The compound 4aa was also prepared using different reaction conditions. Table 1 gives the conditions used and the yield of compound 4aa.

TABLE 1

| Base | Solvent | Temperature | Reaction Time | Yield (%) |
| --- | --- | --- | --- | --- |
| NaH | dimethoxyethane | r.t. | 2 h | 92.4 |
| NaH | tetrahydrofuran | r.t. | 2 h | 91.8 |
| n-BuLi | tetrahydrofuran | r.t. | 2 h | 89.6 |

EXAMPLE 2

2-[3-(1-Phenyl-vinyl)-1,2,5-trioxa-spiro[5.5]undec-9-ylidene]-propionic acid ethyl ester (compound 4ba, Formula 4, Ar=phenyl, R=CH$_3$)

To a stirred and cooled (0° C.) mixture of NaH (0.13 g) in dry dimethoxyethane (20 mL) was added triethylphosphono-2-propionate (0.9 g) and the reaction mixture was stirred at 0° C. for 1 h. To the solution thus obtained was added dropwise a solution of keto trioxane 3a (0.6 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4ba (oil, 0.66 g, 84% yield) as a mixture of E and Z isomers.

EXAMPLE 3

2-[3-(1-Phenyl-vinyl)-1,2,5-trioxa-spiro[5.5]undec-9-ylidene]-butyric acid ethyl ester (compound 4ca, Formula 4, Ar=phenyl, R=CH$_2$CH$_3$)

To a stirred and cooled (0° C.) mixture of NaH (0.04 g) in dry dimethoxyethane (15 mL) was added triethylphosphono-2-butyrate (0.3 g) and the reaction mixture was stirred at 0° C. for 1 h. To the solution thus obtained was added dropwise a solution of keto trioxane 3a (0.2 g) in dry dimethoxyethane (8 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4ca (oil, 0.22 g, 81% yield) as a mixture of E and Z isomers.

EXAMPLE 4

3-(1-Biphenyl-4yl-vinyl)-1,2,5-trioxaspiro[5.5]undec-9-one (compound 3b, Ar=biphenyl)

Allylic alcohol 1b was prepared according to the reported procedure (Singh, C.; Tiwari, P.; Puri, S. K. PCT Patent application No. PCT/1N02/00093, dated 28 Mar. 2002). A solution of allylic alcohol of 1b (1 g) and methylene blue (10 mg) in CH$_2$Cl$_2$: MeCN (1:4, 50 mL) was photooxygenated at −10° C. to 0° C. for 4 h to give β-hydroxyhydroperoxide 2b which was reacted in situ with 1,4-cyclohexanedione (1 g) in presence of concd HCl (5 drops) for 18 h at 0° C. The reaction mixture was worked up as above and concentrated. The crude product was purified by column chromatography on silica gel to furnish trioxane 3b (0.65 g, 42% yield, based on allylic alcohol 1b used), m.p. 104-105° C.

[3-(1-Biphenyl-4-yl-vinyl)-1,2,5-trioxa-spiro[5.5]undec-9-ylidene]-acetic acid ethyl ester (compound 4ab, Formula 4, Ar=4-biphenyl, R=H)

To a stirred and cooled (0° C.) mixture of NaH (0.12 g) in dry dimethoxyethane (20 mL) was added triethylphosphonoacetate (0.8 g) and the reaction mixture was stirred at 0° C. for 1 h. To the solution thus obtained was added dropwise a solution of keto trioxane 3b (0.80 g) in dry dimethoxyethane (15 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4ab (0.89 g, 92.6% yield) as a mixture of E and Z isomers, m.p. 143-145° C.

EXAMPLE 5

2-[3-(1-Biphenyl-4-yl-vinyl)-1,2,5-trioxa-spiro [5.5] undec-9-ylidene]-propionic acid ethyl ester (compound 4bb, Formula 4, Ar=4-biphenyl, R=CH$_3$). ethyl ester (compound 4bb, Formula 4, Ar=4-biphenyl, R=CH$_3$)

To a stirred and cooled (0° C.) mixture of NaH (0.08 g) in dry dimethoxyethane (20 mL) was added triethylphosphono-2-propionate (0.6 g) and the reaction mixture was stirred at 0° C. for 1 h. To the solution thus obtained was added dropwise a solution of keto trioxane 3b (0.50 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4bb (0.52 g, 83.7% yield) as a mixture of E and Z isomers, m.p. 68-70° C.

EXAMPLE 6

3-[1-(4-Chloro-phenyl)-vinyl]-1,2,5-trioxa-spiro[5.5] undecan-9-one (compound 3c, Ar=4-chlorophenyl)

Allylic alcohol 1c was prepared according to the reported procedure (Singh, C. *Tetrahedron Lett.* 1990, 31, 6901). A solution of allylic alcohol of 1c (1 g) and methylene blue (10 mg) in MeCN (50 mL) was photooxygenated at −10° C. to 0° C. for 4 h to give β-hydroxyhydroperoxide 2c which was reacted in situ with 1,4-cyclohexanedione (1.22 g) in presence of concd HCl (5 drops) for 18 h at 0° C. The reaction mixture was worked up as above and concentrated. The crude product was purified by column chromatography on silica gel to furnish trioxane 3c (0.64 g, 38% yield, based on allylic alcohol 1c used), m.p. 72-74° C.

{3-[1-(4-Chloro-phenyl)-vinyl]-1,2,5-trioxa-spiro [5.5]undec-9-ylidene}-acetic acid ethyl ester (compound 4ac, Formula 4, Ar=4-chlorophenyl, R=H)

To a stirred and cooled (0° C.) mixture of NaH (0.09 g) in dry dimethoxyethane (15 mL) was added triethylphosphonoacetate (0.6 g) and the reaction mixture was stirred at 0° C. for 1 h. To the solution thus obtained was added dropwise a solution of keto trioxane 3c (0.50 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4ac (0.56 g, 91.2% yield) as a mixture of E and Z isomers, m.p. 78-80° C.

EXAMPLE 7

2-{3-[1-(4-Chloro-phenyl)-vinyl]-1,2,5-trioxa-spiro [5.5]undec-9-ylidene}-propionic acid ethyl ester (compound 4bc, Formula 4, Ar=4-chlorophenyl, R=CH$_3$)

To a stirred and cooled (0° C.) mixture of NaH (0.05 g) in dry dimethoxyethane (20 mL) was added triethylphosphono-2-propionate (0.5 g) and the reaction mixture was stirred at 0° C. for 1 h. To the solution thus obtained was added dropwise a solution of keto trioxane 3c (0.30 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4bc (oil, 0.33 g, 85.4% yield) as a mixture of E and Z isomers.

EXAMPLE 8

3-[1-(4-Methoxy-phenyl)-vinyl]-1,2,5-trioxa-spiro [5.5]undecan-9-one (compound 3d, Ar=4-methoxyphenyl)

Allylic alcohol 1d was prepared according to the reported procedure (Singh, C. *Tetrahedron Lett.* 1990, 31, 6901). A solution of allylic alcohol of 1d (1 g) and methylene blue (10 mg) in MeCN (50 mL) was photooxygenated at −10° C. to 0° C. for 4 h to give β-hydroxyhydroperoxide 2d which was reacted in situ with 1,4-cyclohexanedione (1.25 g) in presence of concd HCl (5 drops) for 18 h at 0° C. The reaction mixture was worked up as above and concentrated. The crude product was purified by column chromatography on silica gel to furnish trioxane 3d (0.48 g, 28.1% yield, based on allylic alcohol id used) m.p. 74-76° C.

{3-[1-(4-Methoxy-phenyl)-vinyl]-1,2,5-trioxa-spiro [5.5]undec-9-ylidene}-acetic acid ethyl ester (compound 4ad, Formula 4, Ar=4-methoxyphenyl, R=H)

To a stirred and cooled (0° C.) mixture of NaH (0.09 g) in dry dimethoxyethane (15 mL) was added triethylphosphonoacetate (0.6 g) and the reaction mixture was stirred at 0° C. for 1 h. To the solution thus obtained was added dropwise a solution of keto trioxane 3d (0.50 g) in dry dimethoxyethane (15 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4ad (oil, 0.56 g, 91.0% yield) as a mixture of E and Z isomers.

EXAMPLE 9

2-{3-[1-(4-Methoxy-phenyl)-vinyl]-1,2,5-trioxa-spiro[5.5]undec-9-ylidene}-propionic acid ethyl ester (compound 4bd, Formula 4, Ar=4-methoxyphenyl, R=CH$_3$)

To a stirred and cooled (0° C.) mixture of NaH (0.06 g) in dry dimethoxyethane (20 mL) was added triethylphosphono-2-propionate (0.4 g) and the reaction mixture was stirred at 0° C. for 1 h. To the solution thus obtained was added dropwise a solution of keto trioxane 3d (0.30 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4bd (oil, 0.32 g, 84.2% yield) as a mixture of E and Z isomers.

EXAMPLE 10

3-(1-p-Tolyl-vinyl)-1,2,5-trioxa-spiro[5.5]undecan-9-one (compound 3e, Ar=4-methylphenyl)

Allylic alcohol 1e was prepared according to the reported procedure (Singh, C. *Tetrahedron Lett.* 1990, 31, 6901). A solution of allylic alcohol of 1e (1 g) and methylene blue (10 mg) in MeCN (50 mL) was photooxygenated at −10° C. to 0° C. for 4 h to give β-hydroxyhydroperoxide 2e which was reacted in situ with 1,4-cyclohexanedione (1.38 g) in presence of concd HCl (5 drops) for 18 h at 0° C. The reaction mixture was worked up as above and concentrated. The crude product was purified by column chromatography on silica gel to furnish trioxane 3e (0.58 g, 32.7% yield, based on allylic alcohol 1e used), m.p. 66-68° C.

[3-(1-p-Tolyl-vinyl)-1,2,5-trioxa-spiro[5.5]undec-9-ylidene]-acetic acid ethyl ester (compound 4ae, Formula 4, Ar=4-methylphenyl, R=H)

To a stirred and cooled (0° C.) mixture of NaH (0.09 g) in dry dimethoxyethane (15 mL) was added triethylphosphonoacetate (0.6 g) and the reaction mixture was stirred at 0° C. for 1 h. To the solution thus obtained was added dropwise a solution of keto trioxane 3e (0.50 g) in dry dimethoxyethane (15 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4ae (0.56 g, 91.1% yield) as a mixture of E and Z isomers, m.p. 64-66° C.

EXAMPLE 11

2-[3-(1-p-Tolyl-vinyl)-1,2,5-trioxa-spiro[5.5]undec-9-ylidene]-propionic acid ethyl ester (compound 4be, Formula 4, Ar=4-methylphenyl, R=CH$_3$)

To a stirred and cooled (0° C.) mixture of NaH (0.09 g) in dry dimethoxyethane (20 mL) was added triethylphosphono-2-propionate (0.7 g) and the reaction mixture was stirred at 0° C. for 1 h. To the solution thus obtained was added dropwise a solution of keto trioxane 3e (0.50 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4be (oil, 0.53 g, 86.2% yield) as a mixture of E and Z isomers.

EXAMPLE 12

3-[1-(4-Cyclohexyl-phenyl)-vinyl]-1,2,5-trioxa-spiro[5.5]undecan-9-one (compound 3f, Ar=4-cyclohexylphenyl)

Allylic alcohol 1f was prepared according to the reported procedure (Singh, C.; Tiwari, P.; Puri, S. K. PCT Patent application No. PCT/1N02/00093, dated 28 Mar. 2002). A solution of allylic alcohol of 1f (2 g) and methylene blue (20 mg) in MeCN (80 mL) was photooxygenated at −10° C. to 0° C. for 4 h to give β-hydroxyhydroperoxide 2f which was reacted in situ with 1,4-cyclohexanedione (1.94 g) in presence of concd HCl (5 drops) for 18 h at 0° C. The reaction mixture was worked up as above and concentrated. The crude product was purified by column chromatography on silica gel to furnish trioxane 3f (0.98 g, 31.7% yield, based on allylic alcohol 1f used) ), m.p. 56-58° C.

{3-[1-(4-Cyclohexyl-phenyl)-vinyl]-1,2,5-trioxa-spiro[5.5]undec-9-ylidene}-acetic acid ethyl ester (compound 4af, Formula 4, Ar=4-cyclohexylphenyl, R=H)

To a stirred and cooled (0° C.) mixture of NaH (0.06 g) in dry dimethoxyethane (15 mL) was added triethylphosphonoacetate (0.4 g) and the reaction mixture was stirred at 0° C. for 1 h. To the solution thus obtained was added dropwise a solution of keto trioxane 3f (0.40 g) in dry dimethoxyethane (15 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4af (oil, 0.43 g, 89.9% yield) as a mixture of E and Z isomers.

EXAMPLE 13

2-{3-[1-(4-Cyclohexyl-phenyl)-vinyl]-1,2,5-trioxa-spiro[5.5]undec-9-ylidene}-propionic acid ethyl ester (compound 4bf, Formula 4, Ar=4-cyclohexylphenyl, R=CH$_3$)

To a stirred and cooled (0° C.) mixture of NaH (0.05 g) in dry dimethoxyethane (20 mL) was added triethylphosphono-2-propionate (0.4 g) and the reaction mixture was stirred at 0° C. for 1 h. To the solution thus obtained was added dropwise a solution of keto trioxane 3f (0.30 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4bf (oil, 0.30 g, 82.6% yield) as a mixture of E and Z isomers.

EXAMPLE 14

3-(1-Naphthalen-1-yl-vinyl)-1,2,5-trioxa-spiro [5.5] undecan-9-one (compound 3 g, Ar=1-naphthyl)

Allylic alcohol 1g was prepared according to the reported procedure (Singh, C.; Kanchan, R.; Chandra, S. and Puri, S. K. Indian patent application no. 0909/DEL/2003 dated 18 Jul. 2003). A solution of allylic alcohol of 1 g (2 g) and methylene blue (20 mg) in MeCN (80 mL) was photooxygenated at −10° C. to 0° C. for 4 h to give β-hydroxyhydroperoxide 2g which was reacted in situ with 1,4-cyclohexanedione (2.26 g) in presence of concd HCl (5 drops) for 18 h at 0° C. The reaction mixture was worked up as above and concentrated. The crude product was purified by column chromatography on silica gel to furnish trioxane 3 g (0.72 g, 22% yield, based on allylic alcohol 1 g used).

[3-(1-Naphthalen-1-yl-vinyl)-1,2,5-trioxa-spiro[5.5] undec-9-ylidene]-acetic acid ethyl ester (compound 4ag, Formula 4, Ar=1-naphthyl, R=H)

To a stirred and cooled (0° C.) mixture of NaH (0.07 g) in dry dimethoxyethane (15 mL) was added triethylphosphonoacetate (0.4 g) and the reaction mixture was stirred at 0° C. for 1 h. To the solution thus obtained was added dropwise a solution of keto trioxane 3g (0.40 g) in dry dimethoxyethane (15 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4ag (oil, 0.44 g, 90.7% yield) as a mixture of E and Z isomers.

EXAMPLE 15

2-[3-(1-Naphthalen-1-yl-vinyl)-1,2,5-trioxa-spiro [5.5]undec-9-ylidene]-propionic acid ethyl ester (compound 4bg, Formula 4, Ar=1-naphthyl, R=CH$_3$)

To a stirred and cooled (0° C.) mixture of NaH (0.05 g) in dry dimethoxyethane (15 mL) was added triethylphosphono-2-propionate (0.4 g) and the reaction mixture was stirred at 0° C. for 1 h. To the solution thus obtained was added dropwise a solution of keto trioxane 3 g (0.3 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4bg (0.30 g, 80.7% yield) as a mixture of E and Z isomers.

EXAMPLE 16

3-(1-Naphthalen-2-yl-vinyl)-1,2,5-trioxa-spiro[5.5] undecan-9-one (compound 3 h, Ar=2-naphthyl)

Allylic alcohol 1 h was prepared according to the reported procedure (Singh, C.; Kanchan, R.; Chandra, S. and Puri, S. K. Indian patent application no. 0909/DEL/2003 dated 18 Jul. 2003). A solution of allylic alcohol of 1 h (1 g) and methylene blue (10 mg) in MeCN (50 mL) was photooxygenated at −10° C. to 0° C. for 4 h to give β-hydroxyhydroperoxide 2 h which was reacted in situ with 1,4-cyclohexanedione (1.13 g) in presence of concd HCl (5 drops) for 18 h at 0° C. The reaction mixture was worked up as above and concentrated. The crude product was purified by column chromatography on silica gel to furnish trioxane 3 h (0.58 g, 32.7% yield, based on allylic alcohol 1 h used), m.p. 58-60° C.

[3-(1-Naphthalen-2-yl-vinyl)-1,2,5-trioxa-spiro[5.5] undec-9-ylidene]-acetic acid ethyl ester (compound 4ah, Formula 4, Ar=2-naphthyl, R=H)

To a stirred and cooled (0° C.) mixture of NaH (0.08 g) in dry dimethoxyethane (15 mL) was added triethylphosphonoacetate (0.5 g) and the reaction mixture was stirred at 0° C. for 1 h. To the solution thus obtained was added dropwise a solution of keto trioxane 3 h (0.50 g) in dry dimethoxyethane (15 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4ah (0.56 g, 92.1% yield) ) as a mixture of E and Z isomers, m.p. 54-56° C.

EXAMPLE 17

2-[3-(1-Naphthalen-2-yl-vinyl)-1,2,5-trioxa-spiro [5.5]undec-9-ylidene]-propionic acid ethyl ester (compound 4bh, Formula 4, Ar=2-naphthyl, R=CH$_3$)

To a stirred and cooled (0° C.) mixture of NaH (0.09 g) in dry dimethoxyethane (20 mL) was added triethylphosphono-2-propionate (0.6 g) and the reaction mixture was stirred at 0° C. for 1 h. To the solution thus obtained was added dropwise a solution of keto trioxane 3 h (0.50 g) in dry dimethoxyethane (10 mL), while maintaining the temperature of the flask at 0° C. After the addition was complete the resulting solution was stirred for additional half an hour at 0° C. The reaction mixture was worked up as above and concentrated. The crude product was purified by column chromatography on silica gel to furnish spiro trioxane 4bh (0.52 g, 82.6% yield) as a mixture of E and Z isomers.

The antimalarial activity of the test compounds was evaluated in rodent using multi-drug resistant strain of *Plasmodium yoelii Nigeriensis* in Swiss mice.

Random bred Swiss mice of either sex (20±2 gm) were inoculated intraperitoneally with 1×10$^5$ *P. yoelii* (MDR) parasites on day zero. The treatments with test compounds were administered to group of 5 mice each at different dose levels ranging between 24-96 mg/kg/day. The treatment was administered in groundnut oil intramuscularly and orally for 4 consecutive days (day 0-3). Blood smears from experimental mice were observed on day 4 and 7, day 10 and thereafter at regular intervals till day 28 or death of the animal. The parasitaemia level on day 4 was compared with vehicle control group and the percent suppression of parasitaemia in treated groups were calculated.

For determining the curative dose of a compound the treated mice were observed till day 28. The dose at which no parasitaemia develop during the observation period has been reported as the curative dose. The antimalarial activity data is summarized in Table 2.

TABLE 2

ANTIMALARIAL ACTIVITY OF TRIOXANES AGAINST *P. Yoelii* IN MICE.

| Compound | Dose (mg/kg/Day) | Route | % Suppression on Day 4$^a$ | Mice alive on day-28 |
|---|---|---|---|---|
| 3a | 96 | i.m. | 99 | 0/5 |
| 3b | 96 | i.m. | 100 | 1/5 |
| 3c | 96 | oral | 100 | 0/5 |
| 3f | 96 | oral | 100 | 3/5 |
|  | 96 | i.m. | 100 | 2/5 |
| 3g | 96 | oral | 100 | 1/5 |
| 4aa | 48 | oral | 100 | 5/5 |
|  | 96 | i.m. | 99 | 2/5 |
| 4ab | 96 | oral | 100 | 5/5 |
| 4ac | 48 | oral | 100 | 5/5 |
|  | 24 | oral | 100 | 3/5 |
|  | 96 | i.m. | 100 | 5/5 |
|  | 48 | i.m. | 100 | 3/5 |
| 4ad | 96 | oral | 100 | 5/5 |
|  | 96 | i.m. | 100 | 2/5 |
| 4ae | 48 | oral | 100 | 5/5 |
|  | 24 | oral | 100 | 3/5 |
|  | 96 | i.m. | 100 | 5/5 |
|  | 48 | i.m. | 100 | 2/5 |

TABLE 2-continued

ANTIMALARIAL ACTIVITY OF TRIOXANES AGAINST *P. Yoelii* IN MICE.

| Compound | Dose (mg/kg/Day) | Route | % Suppression on Day 4[a] | Mice alive on day-28 |
|---|---|---|---|---|
| 4af | 96 | oral | 100 | 4/5 |
|  | 48 | oral | 100 | 3/5 |
| 4ag | 96 | i.m. | 100 | 5/5 |
| 4ah | 48 | oral | 100 | 5/5 |
|  | 24 | oral | 100 | 1/5 |
|  | 96 | i.m. | 88 | 2/5 |
| 4bb | 96 | oral | 100 | 3/5 |
| 4bf | 96 | oral | 100 | 2/5 |
| β-Arteether | 48 | oral | 100 | 5/5 |
|  | 24 | oral | 100 | 1/5 |
| Chloroquine | 48 | oral | 100 | 2/5 |
|  | 24 | oral | 100 | 0/5 |
| Vehicle Control | — | — | — | 0/15 |

[a]Percent suppression = $[(C - T)/C] \times 100$; where C = parasitaemia in control group, and T = parasitaemia in treated group.

Scheme 1 Reagents and reaction conditions (a) hv, $O_2$, methylene blue, MeCN, <0° C., 4-16 h. (b) 1,4-cyclohexanedione, concd HCl/p-TSA, 0° C. to r.t., 8-18 h. (c) $(OEt)_2$P(O)CHRCO$_2$Et, NaH/n-BuLi, dimethoxyethane/tetrahydrofuran, 0° C. to r.t., 2-3 h.

What is claimed is:

1. A spiro 1,2,4-trioxane of general formula 4,

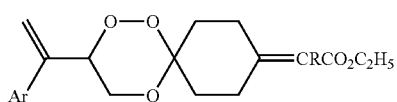

wherein, Ar represents an aryl groups, and R represents hydrogen or an alkyl group.

2. The spiro 1,2,4-trioxane as in claim 1, wherein the aryl group is an unsubstituted or substituted aromatic hydrocarbon, wherein the substituted aromatic hydrocarbon group is substituted with at least one substituent selected from the group consisting of a $C_1$-$C_6$ alkyl, a $C_3$-$C_8$ cycloalkyl, a $C_1$-$C_6$ alkoxy, a halogen and an aromatic hydrocarbon group.

3. The spiro 1,2,4-trioxane as in claim 1, wherein the aryl group is selected from the group consisting of phenyl, 4-biphenyl, 4-chlorophenyl, 4-methoxyphenyl, 4-methylphenyl, 4-cyclohexylphenyl, 1-naphthyl and 2-naphthyl.

4. The spiro trioxane as in claim 1, wherein the alkyl group is selected from the group consisting of methyl, ethyl and propyl.

5. The spiro 1,2,4-trioxanes as in claim 1, wherein the compounds are selected from the group consisting of

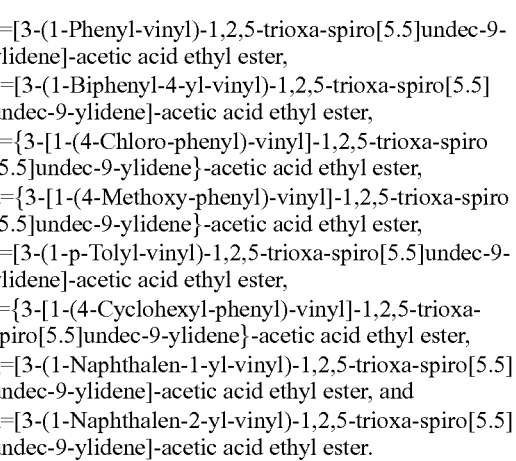

4aa Ar = phenyl
4ab Ar = 4-biphenyl
4ac Ar = 4-chlorophenyl
4ad Ar = 4-methoxyphenyl
4ae Ar = 4-methylphenyl
4af Ar = 4-cyclohexylphenyl
4ag Ar = 1-naphthyl
4ah Ar = 2-naphthyl 4aa=[3-(1-Phenyl-vinyl)-1,2,5-trioxa-spiro[5.5]undec-9-ylidene]-acetic acid ethyl ester, 4ab=[3-(1-Biphenyl-4-yl-vinyl)-1,2,5-trioxa-spiro[5.5]undec-9-ylidene]-acetic acid ethyl ester, 4ac={3-[1-(4-Chloro-phenyl)-vinyl]-1,2,5-trioxa-spiro[5.5]undec-9-ylidene}-acetic acid ethyl ester, 4ad={3-[1-(4-Methoxy-phenyl)-vinyl]-1,2,5-trioxa-spiro[5.5]undec-9-ylidene}-acetic acid ethyl ester, 4ae=[3-(1-p-Tolyl-vinyl)-1,2,5-trioxa-spiro[5.5]undec-9-ylidene]-acetic acid ethyl ester, 4af={3-[1-(4-Cyclohexyl-phenyl)-vinyl]-1,2,5-trioxa-spiro[5.5]undec-9-ylidene}-acetic acid ethyl ester, 4ag=[3-(1-Naphthalen-1-yl-vinyl)-1,2,5-trioxa-spiro[5.5]undec-9-ylidene]-acetic acid ethyl ester, and 4ah=[3-(1-Naphthalen-2-yl-vinyl)-1,2,5-trioxa-spiro[5.5]undec-9-ylidene]-acetic acid ethyl ester.

6. The spiro 1,2,4-trioxanes as claimed in claim 1, wherein the compounds are selected from the group consisting of structural formulas 4ba-4bh:

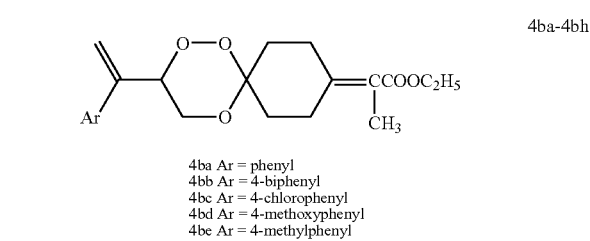

4ba Ar = phenyl
4bb Ar = 4-biphenyl
4bc Ar = 4-chlorophenyl
4bd Ar = 4-methoxyphenyl
4be Ar = 4-methylphenyl
4bf Ar = 4-cyclohexylphenyl
4bg Ar = 1-naphthyl
4bh Ar = 2-naphthyl 4ba=2-[3-(1-Phenyl-vinyl)-1,2,5-trioxa-spiro[5.5]undec-9-ylidene]-propionic acid ethyl, 4bb=2-[3-(1-Biphenyl-4-yl-vinyl)-1,2,5-trioxa-spiro[5.5]undec-9- ylidene]-propionic acid ethyl ester, 4bc=2-{3-[1-(4-Chloro-phenyl)-vinyl]-1,2,5-trioxa-spiro[5.5]undec-9-ylidene}-propionic acid ethyl ester, 4bd=2-{3-[1-(4-Methoxy-phenyl)-vinyl]-1,2,5-trioxa-spiro[5.5]undec-9-ylidene}-propionic acid ethyl ester, 4be=2-[3-(1-p-Tolyl-vinyl)-1,2,5-trioxa-spiro[5.5]undec-9-ylidene]-propionic acid ethyl ester, 4bf=2-{3-[1-(4-Cyclohexyl-phenyl)-vinyl]-1,2,5-trioxa-spiro[5.5]undec-9-ylidene}-propionic acid ethyl ester, 4bg=2-[3-(1-Naphthalen-1-yl-vinyl)-1,2,5-trioxa-spiro[5.5]undec-9-ylidene]-propionic acid ethyl ester, and 4bh=2-[3-(1-Naphthalen-2-yl-vinyl)-1,2,5-trioxa-spiro[5.5]undec-9-ylidene]-propionic acid ethyl ester.

7. The Spiro 1,2,4-trioxane as in claim 1, wherein the compound has the structural formula of 4ca:

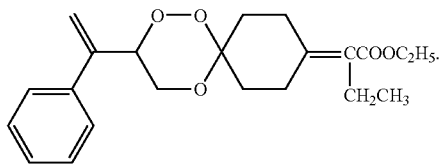

8. The compound of general formula 4 as in claim 1, wherein the compound is effective against parasitaemia up to 100%.

9. A process for the preparation of a spiro 1,2,4-trioxane of general formula 4 comprising the steps of:
   a) photooxygenating of allylic alcohols of formula 1 in presence of a sensitizer and a light source which provides visible light, in an organic solvent at temperature ranging from −10° C. to 0° C. to obtain β-hydroxyhydroperoxide of formula 2,

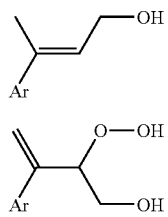

b) reacting β-hydroxyhydroperoxide of formula 2 in-situ with 1,4-cyclohexanedione in the presence of an acid catalyst at temperature 0° C. to for 18 hours to obtain keto trioxanes of general formula 3,

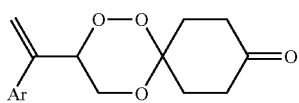

c) reacting the keto trioxanes of step (b) with triethylphosphonoacetate or substituted triethylphosphonoacetate in the presence of a base in an organic solvent at a temperature ranging from 0° C. to 50° C. to obtain spiro 1,2,4-trioxanes of formula 4,

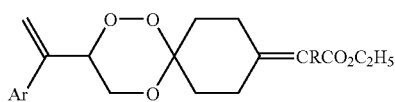

d) isolating and purifying by conventional methods to furnish a spiro 1,2,4-trioxane of formula 4.

10. The process as in claim 9, wherein the aryl group is an unsubstituted or substituted aromatic hydrocarbon, wherein the substituted aromatic hydrocarbon group is substituted with at least one substituent selected from the group consisting of a $C_1$-$C_6$ alkyl, a $C_3$-$C_8$ cycloalkyl, a $C_1$-$C_6$ alkoxy, a halogen and an aromatic hydrocarbon group.

11. The process as in claim 9, wherein the aryl is selected from the group consisting of phenyl, 4-biphenyl, 4-chlorophenyl, 4-methoxyphenyl, and 4-methylphenyl.

12. The process as in claim 9, wherein the sensitizer is methylene blue.

13. The process as in claim 9, wherein the organic solvent in step (a) is selected from the group consisting of aprotic solvents.

14. The process as in claim 13, wherein the aprotic solvent is acetonitrile.

15. The process as in claim 9, wherein the substituted triethylphosphonoacetate is selected from the group consisting of triethylphosphono-2-propionate, and triethylphosphono-2-butyrate.

16. The process as in claim 9, wherein the base in step (c) is selected from sodium hydride, and n-butyl lithium.

17. The process as in claim 9, wherein the organic solvent used in step (c) is selected from the group consisting of tetrahydrofuran, dimethoxyethane, and diethyl ether.

18. The process as in claim 9, wherein the acid catalyst used in step (d) is hydrogen chloride.

19. The process as in claim 9, wherein the compound obtained is selected from the group consisting of the following compounds:
   4aa=[3-(1-Phenyl-vinyl)-1,2,5-trioxa-spiro[5.5]undec-9-ylidene]-acetic acid ethyl-ester,
   4ba=2-[3-(1-Phenyl-vinyl)-1,2,5-trioxa-spiro[5.5]undec-9-ylidene]- propionic acid ethyl ester,
   4ca=2-[3-(1-Phenyl-vinyl)-1,2,5-trioxa-spiro[5.5]undec-9-ylidene]-butyric acid ethyl ester,
   4ab=[3-(1-Biphenyl-4-yl-vinyl)-1,2,5-trioxa-spiro[5.5]undec-9-ylidene]-acetic acid ethyl ester,
   4bb=2-[3-(1-Biphenyl-4-yl-vinyl)-1,2,5-trioxa-spiro[5.5]undec-9-ylidene]-propionic acid ethyl ester,
   4ac={3-[1-(4-Chloro-phenyl)-vinyl]-1,2,5-trioxa-spiro[5.5]undec-9-ylidene}-acetic acid ethyl ester,
   4bc=2-{3-[1-(4-Chloro-phenyl)-vinyl]-1,2,5-trioxa-spiro[5.5]undec-9-ylidene}-propionic acid ethyl ester,
   4ad={3-[1-(4-Methoxy-phenyl)-vinyl]-1,2,5-trioxa-spiro[5.5]undec-9-ylidene}-acetic acid ethyl ester,
   4bd=2-{3-[1-(4-Methoxy-phenyl)-vinyl]-1,2,5-trioxa-spiro[5.5]undec-9-ylidene}-propionic acid ethyl ester,
   4bd=[3-(1-p-Tolyl-vinyl)-1,2,5-trioxa-spiro[5.5]undec-9-ylidene]-acetic acid ethyl ester,
   4be=2-[3-(1-p-Tolyl-vinyl)-1,2,5-trioxa-spiro[5.5]undec-9-ylidene]-propionic acid ethyl ester,
   4af={3-[1-(4-Cyclohexyl-phenyl)-vinyl]-1,2,5-trioxa-spiro[5.5]undec-9-ylidene}-acetic acid ethyl ester,
   4af=2-{3-[1-(4-Cyclohexyl-phenyl)-vinyl]-1,2,5-trioxa-spiro[5.5]undec-9-ylidene}-propionic acid ethyl ester,
   4ag=[3-(1-Naphthalen-1-yl-vinyl)-1,2,5-trioxa-spiro[5.5]undec-9-ylidene]-acetic acid ethyl ester,
   4ag=2-[3-(1-Naphthalen-1-yl-vinyl)-1,2,5-trioxa-spiro[5.5]undec-9-ylidene]-propionic acid ethyl ester,
   4ah=[3-(1-Naphthalen-2-yl-vinyl)-1,2,5-trioxa-spiro[5.5]undec-9-ylidene]-acetic acid ethyl ester, and
   4bh=2-[3-(1-Naphthalen-2-yl-vinyl)-1,2,5-trioxa-spiro[5.5]undec-9-ylidene]-propionic acid ethyl ester.

20. A pharmaceutical composition comprising a pharmaceutically effective amount of compound of formula 4 as in claim 1 and at least one pharmaceutically acceptable diluent and or carrier.

21. A method of treating a subject having malaria, comprising administering to the subject a pharmaceutically effective amount of the pharmaceutical composition as in claim 20.

22. A method of treating a subject having multidrug resistance malaria, comprising administering to the subject a pharmaceutically effective amount of the pharmaceutical composition as in claim 20.

23. The pharmaceutical composition as in claim 20, wherein the pharmaceutical composition has a dose ranging between 24 to 96 mg/kg/day.

24. A method of administering the pharmaceutical composition as in claim 20, comprising administering the composition via intramuscular administration, oral administration, or intraperitoneal administration.

25. The pharmaceutical composition as in claim 20, wherein the composition is effective against parasaitemia up to 100%.

26. A method of treating a subject having malaria, comprising administering to the subject a pharmaceutically effective amount of a composition comprising a compound of formula 4,

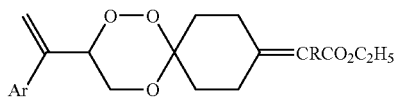

4 wherein, Ar represents an aryl group selected from phenyl, 4-biphenyl, 4-chlorophenyl, 4-methoxyphenyl, 4-methylphenyl, 4-cyclohexylphenyl, 1-naphthyl, 2-naphthyl; R represents hydrogen or an alkyl group, and pharmaceutical acceptable salts thereof.

27. The method as in claim 26, wherein the pharmaceutical composition is administered via intramuscular administration, oral administration, or intraperitoneal administration.

28. The method as in claim 26 wherein the pharmaceutically acceptable amount of a compound of formula 4 is in the range of 24 to 96 mg of a compound of formula 4 per kilogram of body weight of the subject per day.

29. The method as in claim 26, wherein the subject is a human being.

* * * * *